United States Patent
Tegels

(10) Patent No.: US 9,486,194 B2
(45) Date of Patent: Nov. 8, 2016

(54) VASCULAR CLOSURE DEVICE WITH IMPROVED SIDE LOADING

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 0 days.

(21) Appl. No.: 13/787,069

(22) Filed: Mar. 6, 2013

(65) Prior Publication Data

US 2014/0194924 A1   Jul. 10, 2014

Related U.S. Application Data

(60) Provisional application No. 61/749,129, filed on Jan. 4, 2013.

(51) Int. Cl.
*A61B 17/08* (2006.01)
*A61B 17/00* (2006.01)

(52) U.S. Cl.
CPC .. *A61B 17/0057* (2013.01); *A61B 2017/00623* (2013.01); *A61B 2017/00654* (2013.01); *A61B 2017/00898* (2013.01)

(58) Field of Classification Search
CPC ............... A61B 17/0057; A61B 2017/00898; A61B 2017/00672; A61B 2017/00623; A61B 2017/00654
USPC .......... 606/213, 148, 139, 158, 135; 128/41, 128/42; 279/42
See application file for complete search history.

(56) References Cited

U.S. PATENT DOCUMENTS

| | | | | |
|---|---|---|---|---|
| 5,137,288 | A | * | 8/1992 | Starkey et al. ............... 279/42 |
| 5,161,534 | A | * | 11/1992 | Berthiaume ................. 600/434 |
| 5,312,338 | A | * | 5/1994 | Nelson et al. ............... 604/528 |
| 5,324,298 | A | * | 6/1994 | Phillips et al. .............. 606/148 |
| 6,699,261 | B1 | | 3/2004 | Cates et al. |
| 7,706,861 | B2 | * | 4/2010 | Windheuser et al. ........ 600/434 |
| 2005/0020899 | A1 | * | 1/2005 | Chernomorsky et al. .... 600/407 |
| 2006/0099238 | A1 | | 5/2006 | Khosravi et al. |
| 2006/0178682 | A1 | * | 8/2006 | Boehlke ........................ 606/148 |
| 2010/0292532 | A1 | * | 11/2010 | Kadykowski et al. ....... 600/104 |
| 2012/0143215 | A1 | | 6/2012 | Corrao et al. |
| 2012/0245624 | A1 | * | 9/2012 | Glazier et al. ............... 606/213 |

OTHER PUBLICATIONS

PCT International Search Report for International Application No. PCT/US2013/029239, mailed Oct. 1, 2013 (7 pp.).

* cited by examiner

*Primary Examiner* — Todd E Manahan
*Assistant Examiner* — Erich Herbermann
(74) *Attorney, Agent, or Firm* — Holland & Hart

(57) ABSTRACT

A tissue puncture closure device includes a vessel locator and a sealing plug delivery member. The vessel locator includes an expandable member. The sealing plug delivery member includes a carrier tube, a sealing plug, and a locking member. The carrier tube includes a distal end and a side opening, the side opening extending proximally from the distal end along at least a portion of a length of the carrier tube to provide lateral insertion of the vessel locator into an interior of the carrier tube. The sealing plug includes a lumen and a slot extending from a distal end to a proximal end of the sealing plug, wherein the slot provides lateral access of the vessel locator into the lumen. The locking member is operable to retain the vessel locator within the sealing plug delivery member.

23 Claims, 15 Drawing Sheets

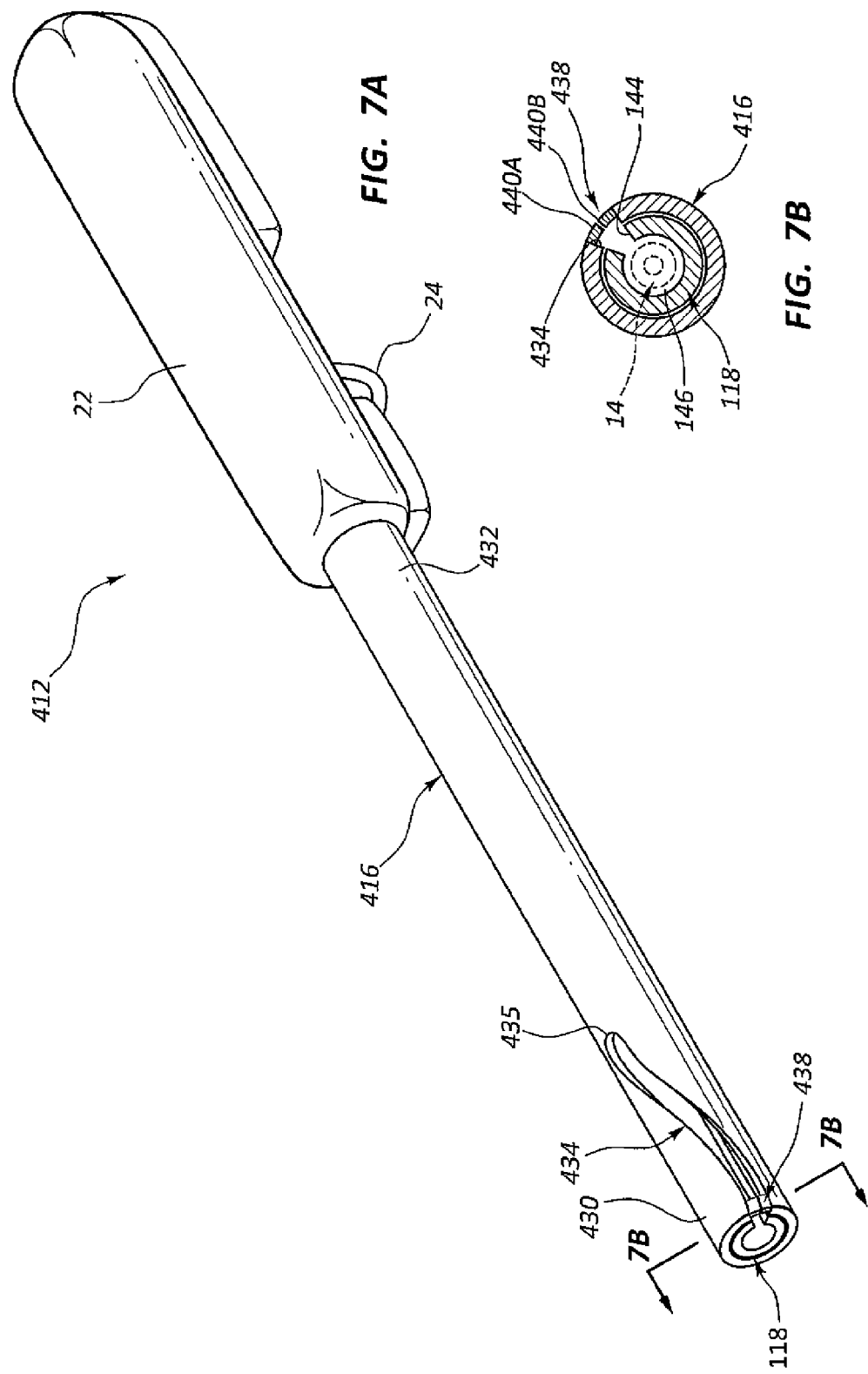

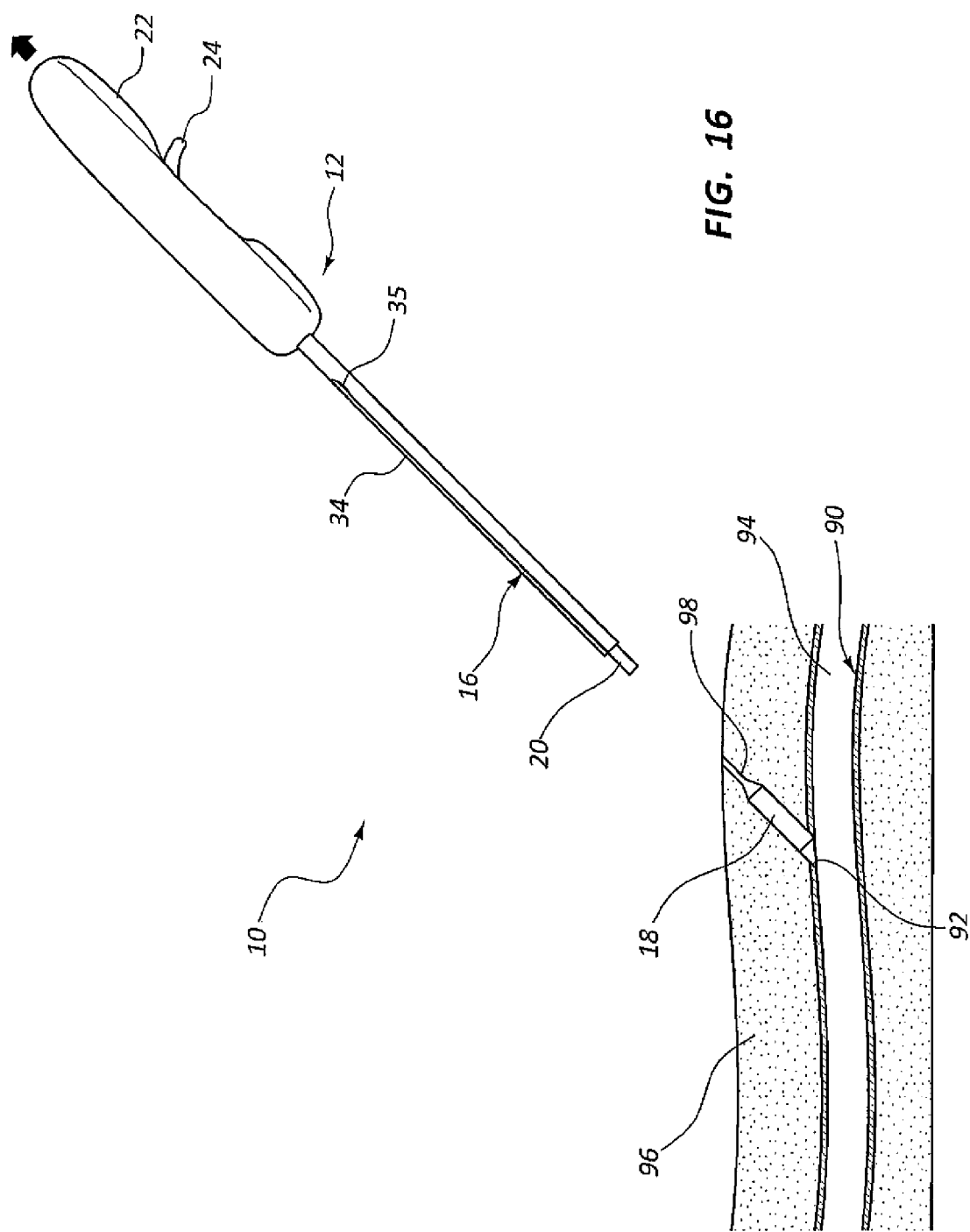

VASCULAR CLOSURE DEVICE WITH IMPROVED SIDE LOADING

RELATED APPLICATION

This claims the benefit of U.S. Provisional Application No. 61/749,129, filed 4 Jan. 2013, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices.

Typical closure devices such as the ones described in the above-mentioned patents place a sealing plug at the tissue puncture site. Deployment of the sealing plug may involve ejecting the sealing plug from within the closure device sheath to a location in alignment with and adjacent to the tissue puncture along an outer surface of the vessel and within a percutaneous tissue tract. Mounting the closure device onto a proximal end of the guidewire and advancing the closure device to the tissue puncture site may require both of the operator's hands. However, in at least some treatment procedures, one of the operator's hands is used to apply and maintain pressure to the patient adjacent to the tissue puncture to provide hemostasis and hold the guidewire within the vessel. Releasing the operator's hand from applying pressure to the patient may result in complications in the procedure. Opportunities exist for improvements in this technical area.

SUMMARY

One aspect of the present disclosure relates to a tissue puncture closure device that includes a vessel locator and a sealing plug delivery member. The vessel locator includes an expandable member. The sealing plug delivery member includes a carrier tube, a sealing plug, and a locking member. The carrier tube includes a distal end and a side opening, the side opening extending proximally from the distal end along at least a portion of a length of the carrier tube to provide lateral insertion of the vessel locator into an interior of the carrier tube. The sealing plug includes a lumen and a slot extending from a distal end to a proximal end of the sealing plug, wherein the slot provides lateral access of the vessel locator into the lumen. The locking member is operable to retain the vessel locator within the sealing plug delivery member.

The sealing plug delivery member may include an actuator operable to deposit the sealing plug adjacent to a vessel puncture to seal the vessel puncture, wherein the actuator retracts the carrier tube relative to the sealing plug to deposit the sealing plug adjacent to the vessel puncture. The sealing plug delivery member may include an actuator operable to deposit the sealing plug adjacent to a vessel puncture to seal the vessel puncture, wherein the actuator advances the sealing plug out of the carrier tube to deposit the sealing plug adjacent to the vessel puncture. The locking member may rotate between a first position covering at least a portion of one of the side opening of the carrier tube and the slot of the sealing plug, and a second position removed from covering the side opening and slot.

The locking member may include a deflectable member position at the side opening. The side opening and slot may be aligned radially. The slot may have a non-linear shape along a length of the sealing plug. The slot may have a helical shape along a length of the sealing plug. The slot may extend diagonally along a length of the sealing plug. The locking member may include a one-way opening. The locking member may be positioned at the distal end of the carrier tube.

Another aspect of the present disclosure relates to a tissue puncture closure device adapted for insertion into and sealing of a tissue puncture in a tissue wall. The tissue puncture closure device includes a sealing plug delivery member having a carrier tube, a sealing plug, a locking member, and a placement member. The carrier tube includes a tube slot extending through a sidewall of the carrier tube and extending proximally from a distal end of the carrier tube. The sealing plug is positioned in the carrier tube and has a lumen and a plug slot extending through a sidewall of the sealing plug. The plug slot extends along a length of the sealing plug and at least a portion thereof is aligned radially with the tube slot. The locking member controls passage of an elongate locator member through the tube slot. The placement member is positioned in the carrier tube at a location proximal of the sealing plug. The placement member is operable to position the sealing plug adjacent to the tissue puncture.

The plug slot may have a non-linear shape. The sealing plug may be cylindrical shaped with a circular cross-section. The locking member may include a sleeve positioned on the carrier tube, wherein the sleeve is rotatable between locked and unlocked positions. The locking member may include a flexible tab positioned within the tube slot at a distal end of the carrier tube. The sealing plug delivery member may include an actuator operable to retract the carrier tube relative to the sealing plug. The sealing plug may be rotatable within the carrier tube as the elongate locator member is inserted into the plug slot. The tube slot may terminate distal of a proximal end of the carrier tube.

Another aspect of the present disclosure relates to a method of sealing a vessel puncture in a wall of a vessel that is accessible through a percutaneous incision. The method includes providing a closure device and a vessel locator, wherein the closure device includes a sealing plug and a carrier tube. The carrier tube includes a tube slot formed in a sidewall thereof. The sealing plug includes a plug slot formed in a sidewall thereof and positioned in the carrier tube. The method includes advancing the vessel locator through the percutaneous incision and into the vessel puncture, anchoring the vessel locator within the vessel, laterally inserting the vessel locator through the tube slot and the plug slot, advancing the closure device along the vessel locator to the vessel puncture, and depositing the sealing plug adjacent to the vessel puncture to seal the vessel puncture.

The closure device may include a locking member, and the method includes operating the locking member to retain the vessel locator within the carrier tube. Operating the locking member my include rotating the locking member relative to the carrier tube. Operating the locking member may include providing a one-way opening into the tube slot to restrict removal of the vessel locator from the carrier tube. The plug slot may have a non-linear shape along a length of the sealing plug, and laterally inserting the vessel locator includes rotating the sealing plug relative to the carrier tube.

Additional advantages and novel features will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and are not intended to be limiting.

FIG. 7A is a perspective view of another example sealing plug delivery device in accordance with the present disclosure.

FIG. 7B is a cross-sectional view of the sealing plug delivery device of FIG. 7A taken along cross-section indicators 7B-7B.

FIGS. 10-16 show example method steps for sealing a vessel puncture using a tissue puncture closure device that includes the sealing plug delivery device of FIGS. 1A and 1B.

Throughout the drawings, identical reference numbers designate similar, but not necessarily identical, elements.

DETAILED DESCRIPTION

Figure 1:
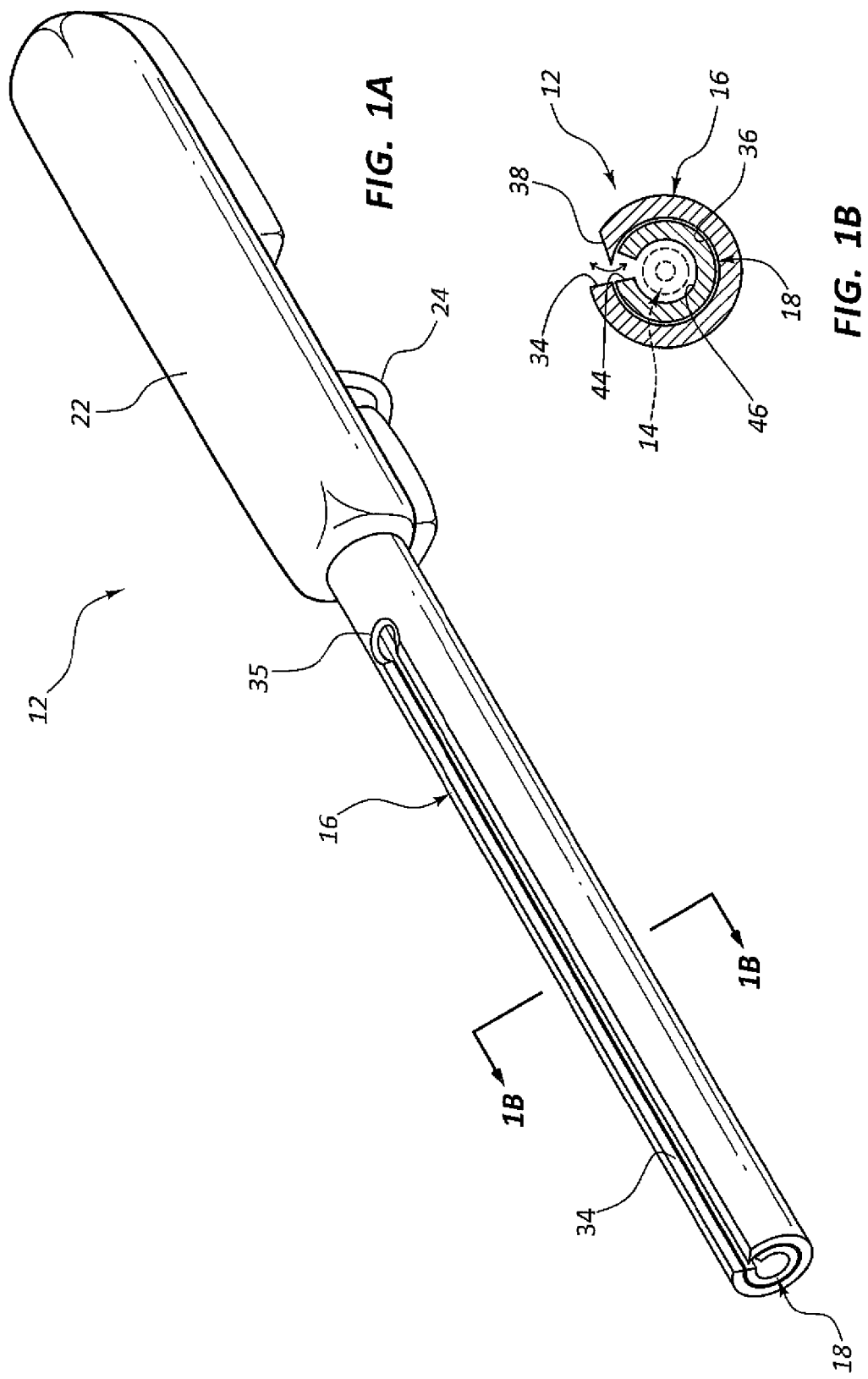
FIG. 1A is a perspective view of an example sealing plug delivery device in accordance with the present disclosure.
FIG. 1B is a cross-sectional view of the sealing plug delivery device of FIG. 1A.

As mentioned above, vascular procedures are conducted throughout the world and require access to a vessel through a puncture. Often, the vessel is a femoral artery. To close the puncture following completion of the procedure, a closure device may be used to position a sealing plug within a percutaneous incision adjacent to the puncture. The closure device may be advanced over a guidewire or other vessel locator device that is positioned extending through the percutaneous incision and the puncture. The guidewire may include a temporary anchor feature that is expandable within the vessel to provide an anchoring, locating and/or sealing function internal to the vessel, and returns to an unexpanded state for removal of the guidewire through the percutaneous incision and puncture after the sealing plug has been positioned in the percutaneous incision.

Advancing the closure device over the guidewire to the percutaneous incision typically involves inserting a proximal end of the guidewire into a distal opening of the dilator and closure device at a location that is spaced relatively far from the percutaneous incision. Because of the relatively flexible nature of the guidewire and the distance from the percutaneous incision to the proximal end of the guidewire, both of the operator's hands are usually needed to mount the closure device to the guidewire and withdraw the dilator and closure device from off the proximal end of the guidewire. If both of the operator's hands are needed to mount the closure device to the guidewire, it may be difficult for the operator to perform other aspects of the patient treatment such as applying pressure to the patient adjacent to the percutaneous incision to create hemostasis and/or retain a distal end of the guidewire in the puncture.

Some guidewires include a temporary expandable anchor that is positioned near a distal end portion of the guidewire. The anchor may have a collapsed state or position that permits the anchor and distal end of the guidewire to pass through the incision and puncture (i.e., into a vessel lumen). The guidewire may include actuator features positioned outside of the patient that are operable to move the anchor into an expanded position. Alternatively, the guidewire may include a hub or port used to connect the expandable anchor to a source of inflation fluid. A size of the anchor when in the expanded state limits withdrawal of the anchor out of the puncture. The anchor may provide a sealing and anchoring function when in the expanded state. The actuator features of the guidewire are typically sized small enough that the closure device may be advanced over the proximal end of the guidewire with the actuator features passing through an interior of the closure device. Actuator features of this relatively small size may be difficult for the operator to handle when, for example, the operator moves the actuator features to expand and collapse the anchor during treatment of the patient.

The devices and methods of the present disclosure may provide the operator with the ability to advance and withdraw the closure device over the guidewire using one hand as part of treating the patient. The operator's other hand may be used to maintain pressure on the patient adjacent the tissue tract, for example, to limit blood flow through a vessel of the patient being treated or to hold a distal end of the guidewire within the vessel being treated.

Further, the devices and methods disclosed herein may provide the option of using anchor actuator features of increased size that may be easier for the operator to handle when expanding and contracting the anchor.

In at least one example, the closure device is configured to mount to the guidewire in a lateral direction rather than solely in an axial direction. Lateral mounting of the closure device may make it possible to mount the closure device to the guidewire at a location distal of the anchor actuator features so that the anchor actuator features do not have to pass through interiors of the closure device and sealing plug.

Many types of anchor structures may be used with the locator wire assemblies described herein. In at least one example, the anchor comprises an expandable basket or cage-type structure that is covered with, for example, a flexible membrane. A wire actuator that extends along at least a portion of the length of the locator wire assembly is used to expand and contract the basket or cage structure within the membrane. Other anchor constructions and actuator arrangements are possible for use in the locator wire assemblies described herein. In one example, an inflation balloon is used instead of a mechanically actuated anchor member. In other examples, the guidewire does not include an anchor member, but does include a handle or connector at its proximal end for improved ease in handling the guidewire.

While the vascular instruments shown in the attached figures and described below may include procedural sheaths and puncture sealing devices, the application of principles described herein are not limited to the specific devices shown. The principles described herein may be used with any medical device. Therefore, while the description below is directed primarily to vascular procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "tube" is an elongated device with a passageway. The passageway may be enclosed or open (e.g., a trough). A "lumen" refers to any open space or cavity in a device or bodily organ, especially in a blood vessel. The words "including" and "having," as used in the specification, including the claims, have the same meaning as the word "comprising."

Figure 2:
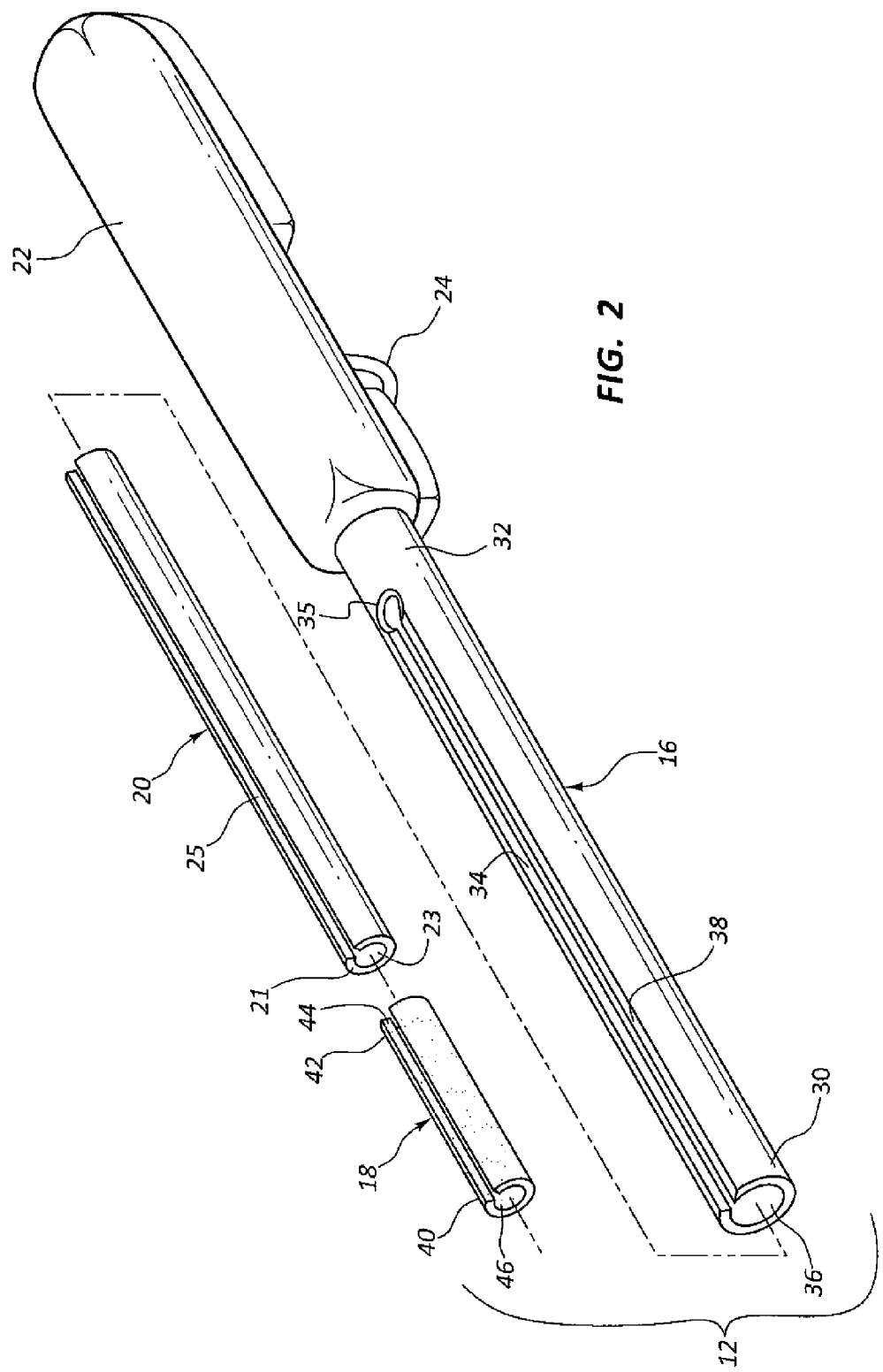
FIG. 2 is an exploded perspective view of the sealing plug delivery device of FIG. 1A.
Figure 3:
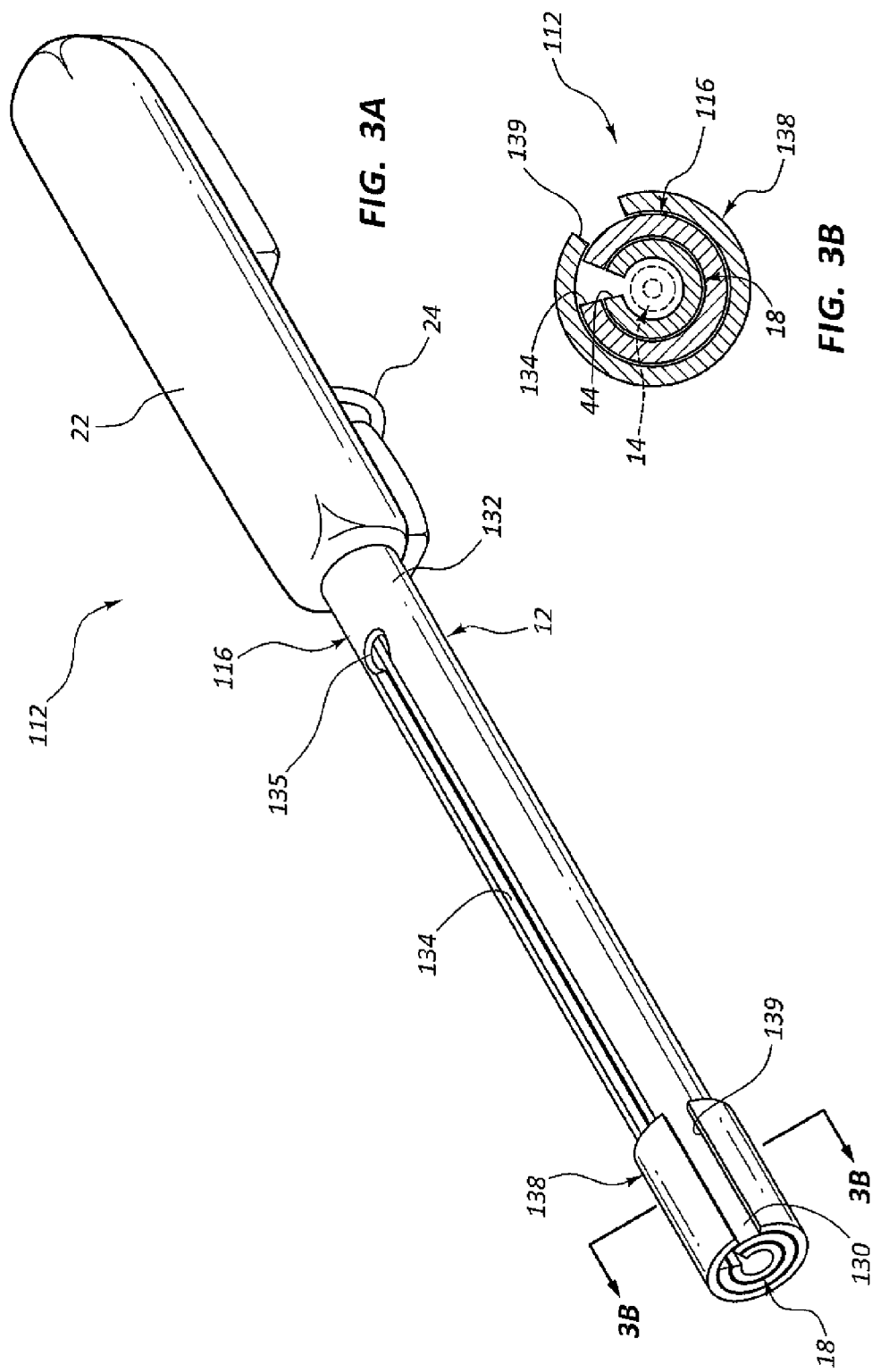
FIG. 3A is a perspective view of another example sealing plug delivery device in accordance with the present disclosure.
FIG. 3B is a cross-sectional view of the example sealing plug delivery device of FIG. 3A taken along cross-section indicators 3B-3B.
Figure 4:
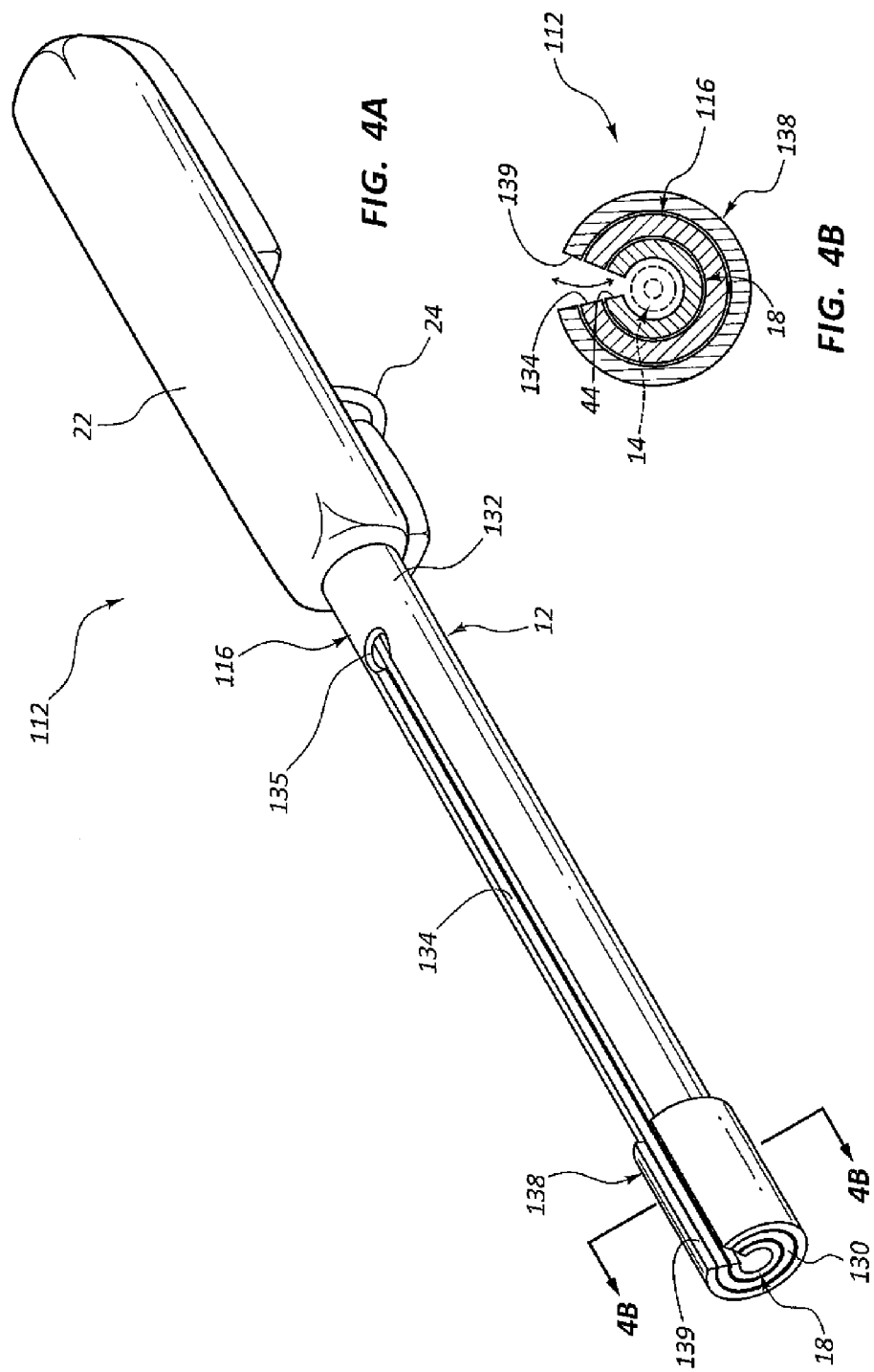
FIG. 4A is a perspective view of another example sealing plug delivery device in accordance with the present disclosure.
FIG. 4B is a cross-sectional view of the sealing plug delivery device of FIG. 4A taken along cross-section indicators 4B-4B.

Referring now to FIGS. 1A-2, an example sealing plug delivery device 12 is shown including a carrier tube 16, a sealing plug 18, a placement member 20, a housing 22, and a tube retractor 24. The sealing plug 18 and placement member 20 are positioned within the carrier tube 16. The carrier tube 16 is connected to housing 22. The tube retractor 24 may operate to either retract the carrier tube 16 relative to the sealing plug 18 and placement member 20 to deposit the sealing plug at a vessel puncture, or advance the placement member 20 to eject the sealing plug 18 out of a distal end of the carrier tube 16 to deposit the sealing plug at the vessel puncture.

The carrier tube 16 may include distal and proximal end portions 30, 32, a tube slot 34, a tube lumen 36, and a locking member 38 (see FIGS. 1B and 2). The tube slot 34 extends from a distal surface at the distal end portion 30 to a proximal end 35. Typically, the proximal end 35 is positioned distal of the housing 22. The proximal end 35 may operate as a rapid exchange port that provides an exit point for an elongate member such as a guidewire or a vessel locator to pass out of the carrier tube 16 without having to pass through the housing 22.

The tube slot 34 may extend along at least a portion of a length of the carrier tube 16. In one example, the tube slot 34 extends along substantially an entire length of the carrier tube 16. Other examples include tube slots that have a shorter length such as a length that extends along only the distal end portion 30.

The tube slot 34 extends through a side wall of the carrier tube 16. The tube slot 34 may extend from an exterior surface (e.g., an outer peripheral surface) of the carrier tube 16 into the tube lumen 36. The tube slot 34 may provide a lateral access point or lateral insertion point or opening into the tube lumen 36. Insertion into the tube slot may be referred to as a insertion in a lateral direction or a radially inward direction.

The carrier tube 16 may include at least one feature that controls access into and out of the tube slot 34. For example, the locking member 38 may operate to permit lateral access into the tube lumen 36 through the tube slot 34 while resisting lateral movement out of the tube lumen 36 through the tube slot 34. The locking member 38 is shown in at least FIG. 1B as a flexible tab that protrudes into the tube slot 34. The locking member 38 may flex or deform radially inward when inserting a device laterally through the tube slot 34 and into the tube lumen 36. The locking member 38 may have a tapered construction that helps direct the object through the tube slot 34 and into the tube lumen 36. An opposite surface of the locking member 38 may be untapered and have greater stiffness (e.g., resistance to deforming or deflecting radially outward) thereby helping hold the object within the tube lumen 36.

The locking member 38 may be positioned at any desired location along a length of the tube slot 34. In one example, the locking member 38 extends along substantially an entire length of the tube slot 34. Other arrangements are possible in which the locking member 38 is positioned at only specific locations along the length of the tube slot 34 (e.g., at the distal and proximal end portions 30, 32 or at any desired spaced apart location along the length of the tube slot 34).

The locking member 38 may be integrally formed as a single piece with the remaining portions of the carrier tube 16. In other arrangements, the locking member 38 is formed as a separate piece that is attached to the carrier tube 16 using, for example, bonding, welding or other connection methods.

The locking member 38 may extend into the tube slot 34 from one side edge of the tube slot 34, as shown in FIG. 1B. Other arrangements are possible in which portions of the locking member 38 extend from both side edges of the tube slot 34. In still other arrangements, the locking member 38 is positioned on either an exterior surface or interior surface of the carrier tube 16. The locking member 38 may cover or extend into a portion of the tube slot 34.

The sealing plug 18 includes distal and proximal ends 40, 42, a plug slot 44, and a plug lumen 46 (see FIG. 2). The sealing plug may comprise a resorbable material such as, for example, collagen. The sealing plug may expand in response to being exposed to a liquid such as blood. The sealing plug 18 may expand to close the plug slot 44 after the sealing plug 18 is removed from the carrier tube 16. The sealing plug 18, when expanded, may also close the plug lumen 46. The sealing plug 18 may change states upon being exposed to a liquid. In one example, the sealing plug 18 changes from a solid state to a gel or semi-gel state upon being exposed to a liquid.

The plug slot 44 may extend an entire length of the sealing plug 18. In one example, the plug slot 44 extends from a distal surface at the distal end 40 to a proximal surface at the proximal end 42. The plug slot 44 is shown in FIG. 2 having a substantially linear shape that is arranged parallel with a longitudinal dimension (e.g., longitudinal axis) of the sealing plug 18.

The plug slot 44 may extend from an outer surface of the sealing plug 18 into the plug lumen 46. The plug slot 44 may extend from an outer peripheral surface in a lateral direction (also referred to as a radially inward direction) into the plug lumen 46. The plug slot 44 may provide access into the plug lumen 46 at a location spaced between the distal and proximal ends 40, 42.

The sealing plug 18 is shown in the figures having a generally cylindrical shape with a circular cross-section. The plug lumen 46 may have a corresponding cylindrical shape with a circular cross-section. The sealing plug 18 may have any desired cross-sectional shape and length. Typically, the shape of the sealing plug 18 substantially matches a shape of the tube lumen 36 of the carrier tube 16. For example, FIG. 1B shows the tube lumen 36 having a generally circular cross-sectional shape and is sized for receiving the sealing plug 18, which also has a cylindrical shape with circular cross-section.

Figure 9A:
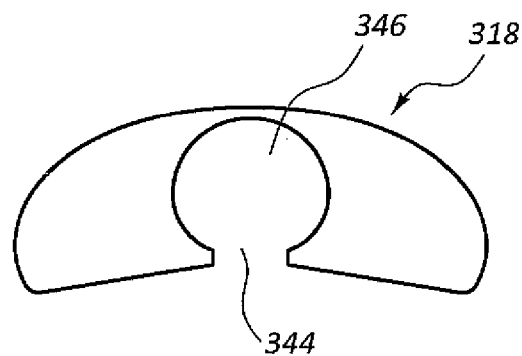
FIGS. 9A-9C are end views of example sealing plugs for use with the sealing plug delivery devices of FIGS. 1-7B.
Figure 9B:
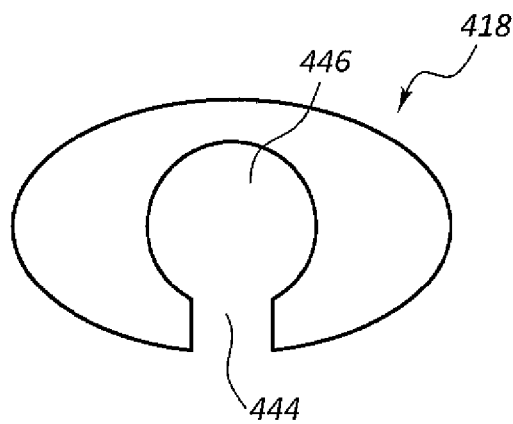
Figure 9C:
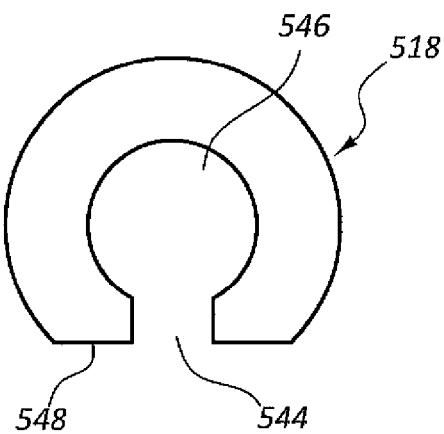
Figure 10:
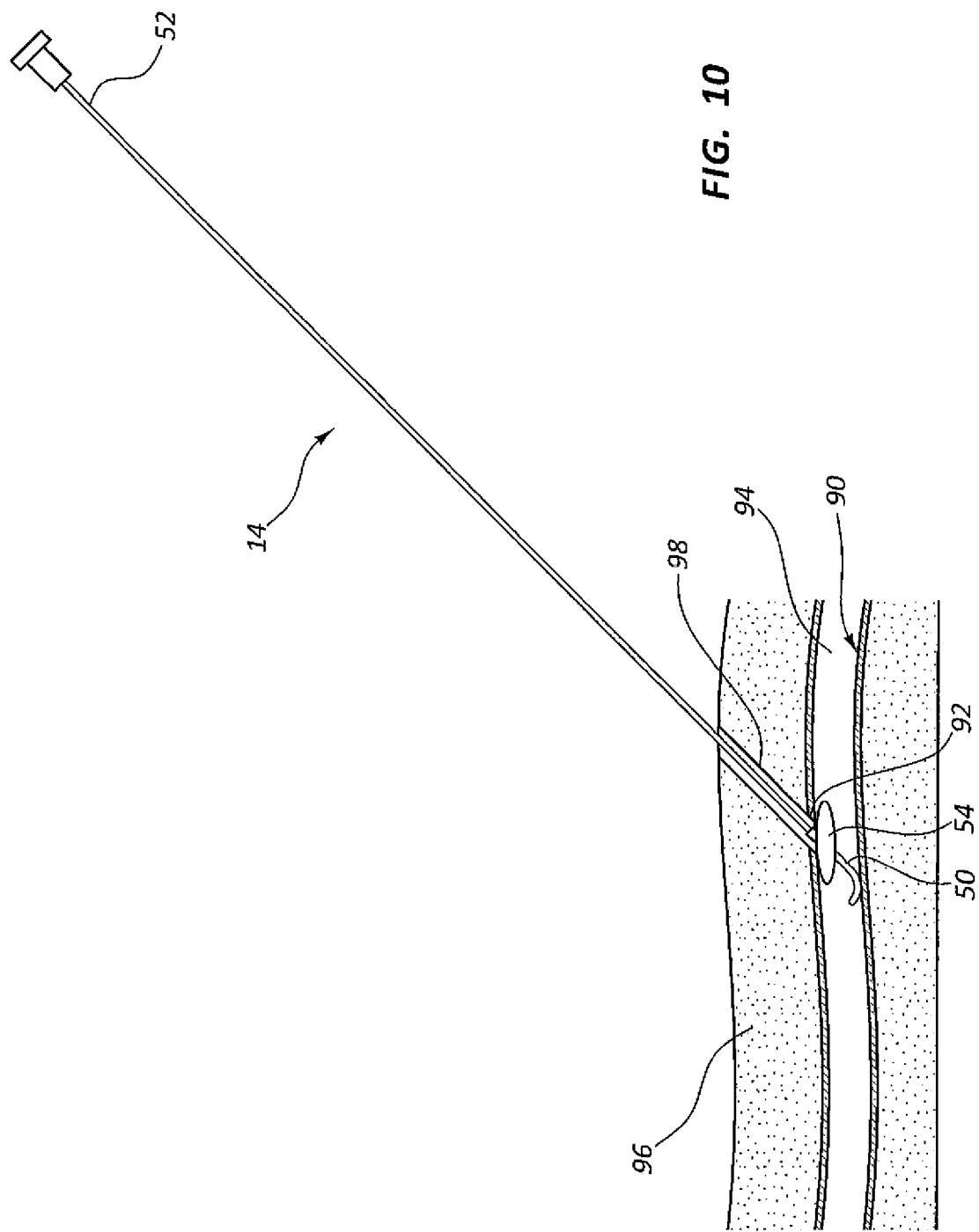

Many other cross-sectional shapes are possible for the sealing plug 18. FIGS. 9A-9C show several alternative cross-sectional shapes for the sealing plug. FIG. 9A shows a sealing plug 318 having a generally crescent cross-sectional shape. The sealing plug 318 includes a plug lumen 346 and a plug slot 344 providing access from an outer surface of the sealing plug into the plug lumen 346 in a lateral direction.

FIG. 9B shows another example sealing plug 418 having an oval cross-sectional shape. The sealing plug 418 includes a plug slot 444 that provides lateral access into a plug lumen 446. The plug slot 444 may be oriented along an outer periphery of the sealing plug 418 at a location where a thickness of the sealing plug is at its minimum amount. The plug lumen 446 may have any desired cross-sectional shape. For example, the plug lumen 446 may have an oval shape that matches the oval outer peripheral shape of the sealing plug 418.

FIG. 9C shows a sealing plug 518 that includes a plug slot 544 that provides lateral access into a plug lumen 546. The sealing plug 518 may include a flat surface 548 at a location around a periphery of the sealing plug 518 and along at least a portion of a length of the sealing plug 518. The flat surface 548 may minimize a thickness of the sealing plug through which the plug slot 544 extends to reach the plug lumen 546.

Many other cross-sectional shapes, sizes and configurations are possible for the sealing plugs disclosed herein. The plug slot and plug lumen of each sealing plug configuration may have any shape or size.

Figure 8A:
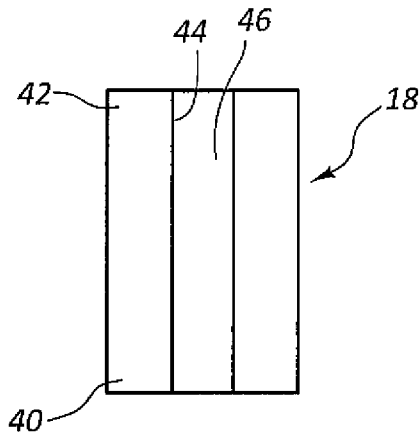
FIGS. 8A-8C are side views of example sealing plugs for use with the sealing plug delivery devices of FIGS. 1-7B.
Figure 8B:
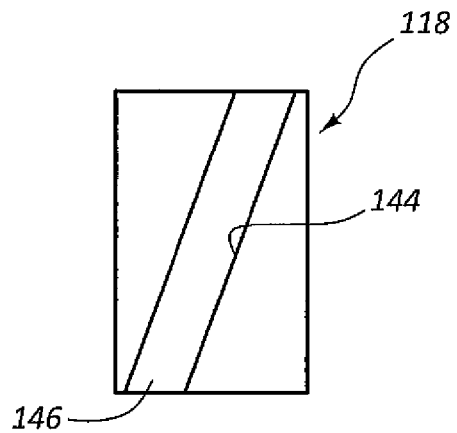
Figure 8C:
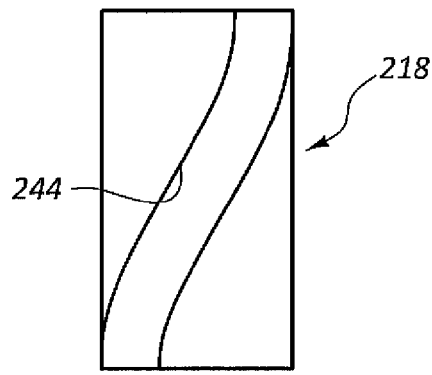

The plug slot 44 of the sealing plug 18 may have an arrangement that is nonparallel with a length dimension of the sealing plug or that includes a non-linear shape. FIG. 8A shows a side view of the sealing plug 18. The plug slot 44 of the sealing plug 18 has a linear shape and is arranged parallel with a length dimension of the sealing plug 18. FIG. 8B shows another example sealing plug 118, which includes a plug slot 144 arranged diagonally along the length of the sealing plug 118. FIG. 8C shows another example sealing plug 218 having a plug slot 244 with a helical shape.

At least a portion of the plug slot 44 is aligned with the tube slot 34 in a radial direction when the sealing plug delivery device 12 is assembled, as shown in FIGS. 1A and 1B. The alignment of tube slot 34 with plug slot 44 permits lateral access into the plug lumen 46 for a device such as, for example, a vessel locator 14 (an example of which is shown in FIGS. 10-16). The shape and orientation of tube slot 34 may be substantially the same as the shape of plug slot 44 along a length of the sealing plug 18 so that the vessel locator may be inserted laterally through tube slot 34 and plug slot 44 along an entire length of the sealing plug 18 without relative rotation between the sealing plug 18 and carrier tube 16. In other examples, the vessel locator may be inserted through the tube slot 34 into a portion of the plug slot 44 (e.g., a distal end 40), and the sealing plug 18 rotates relative to the carrier tube 16 as the vessel locator 14 is inserted through the remaining portions of the plug slot 44 (e.g., up to the proximal end 42). Relative rotation between a sealing plug 18 and carrier tube 16 may be useful or required when using, for example, the sealing plug 118 having a diagonal oriented plug slot 144 with the carrier tube 16 having a linear tube slot 34 that is oriented parallel with a length dimension of the carrier tube 16.

Referring again to FIG. 2, the placement member 20 includes a distal end 21, a lumen 23, and slot 25. The placement member 20 may be positioned within the carrier tube 16 at an orientation in which the slot 25 is aligned with the tube slot 34. The slot 25 may also be aligned with a portion of the plug slot 44. The slot 25 may have any desired length and may extend from the distal end 21 at least to a position of the proximal end 35 of the tube slot 34. The slot 25 may provide lateral access through the placement member 20 and into the lumen 23.

The placement member 20 may be used to position the sealing plug 18 adjacent to a vessel puncture, as described in further detail below. In one example, the placement member 20 maintains an axial position of the sealing plug 18 while the carrier tube 16 is retracted into the housing 22. In another example, the placement member 20 is advanced distally to eject the sealing plug 18 from the distal end portion 30 of the carrier tube 16. The placement member 20 may be moved axially using the tube retractor 24. Alternatively, the tube retractor 24 may move the carrier tube 16 relative to the placement number 20.

In other arrangements, the placement number 20 does not include at least one of the lumen 23 and the slot 25. An elongate member such as vessel locator 14, which is inserted through the tube slot 34, may extend through the plug slot 44 into the plug lumen 46 while remaining along an exterior surface of the placement member 20 along at least a portion of the length of the placement member 20. In still further embodiments, the sealing plug delivery device 12 does not include a placement member 20, but rather uses other features and functionality to remove the sealing plug 18 from the carrier tube 16.

Referring now to FIGS. 3A-4B, another example sealing plug delivery device 112 is shown having an alternative locking member 138. The sealing plug delivery device 112 includes a carrier tube 116, a sealing plug 18 and a locking member 138. The carrier tube 116 includes a tube slot 134 that is free of obstructions as shown in FIG. 3B. The tube slot 34 is aligned with a plug slot 44 of the sealing plug 18 to provide lateral access into the plug lumen 46. The locking member 138 rotates relative to the carrier tube 116 to control access into at least a portion of the tube slot 134.

FIGS. 3A and 3B show the locking member 138 in a first rotated position relative to the carrier tube 16 to block access to a portion of the tube slot 134. FIGS. 4A and 4B show the locking member 138 in a second rotated position in which a locking slot 139 of the locking member 138 is aligned with the tube slot 134 to permit lateral access through the tube slot 134. As clearly shown in these figures, the locking member 138 rotates around a central longitudinal axis of the vessel locator 14, the sealing plug 18, and/or the carrier tube 116. An elongate member such as the vessel locator 14 may pass laterally through the locking slot 139, tube slot 134 and plug slot 44 when the locking member 138 is in the open or second rotated position of FIGS. 4A and 4B.

The locking member 138 may be positioned at any location along a length of the carrier tube 116. FIGS. 3A-4B show the locking member 138 positioned at the distal end portion 130 of the carrier tube 116. A remaining length of the tube slot 134 arranged proximal of the locking member 138 may have little or no restriction for lateral movement into and out of the tube slot with an elongate member such as the vessel locator 14.

Figure 5:
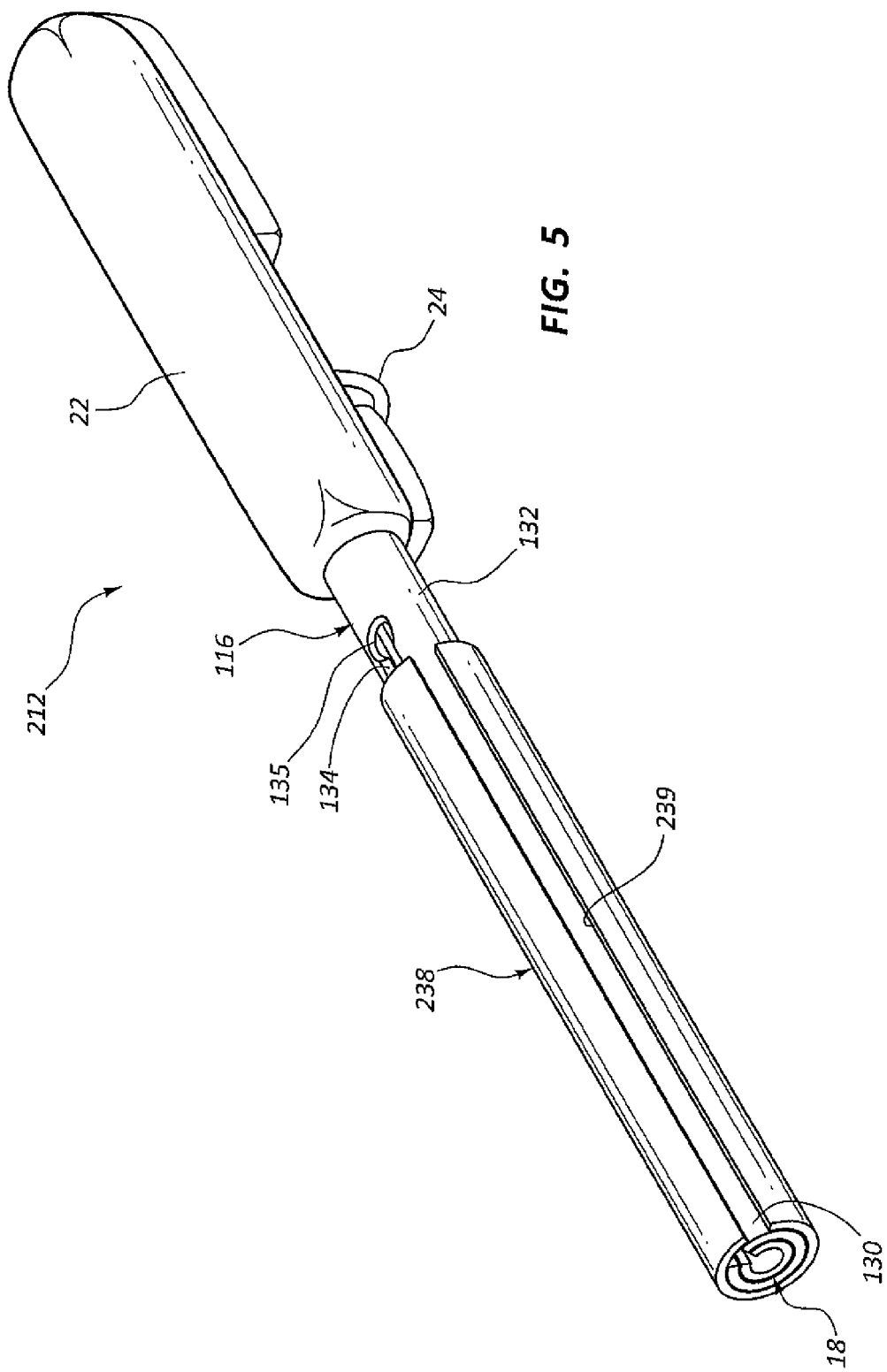
FIG. 5 is a perspective view of another example sealing plug delivery device in accordance with the present disclosure.

FIG. 5 shows an alternative shape for the rotatable locking member. FIG. 5 illustrates a sealing plug delivery device 212 that includes a carrier tube 116, a sealing plug 18, and a locking member 238. The carrier tube 116 includes a tube slot 134. The locking member 238 includes a locking slot 239 that extends along substantially the entire length of the locking member 238. The locking member 238 may have a length that extends along substantially an entire length of the tube slot 134. The locking member 238 may extend from a distal end portion 130 to a proximal end portion 132 of the carrier tube 116.

The locking member 238 may rotate between a first or closed position in which the locking slot 239 is rotated out of alignment with the tube slot 134, and a second or open position in which the locking slot 239 is radially aligned with the tube slot 134 (not shown).

Figure 6:
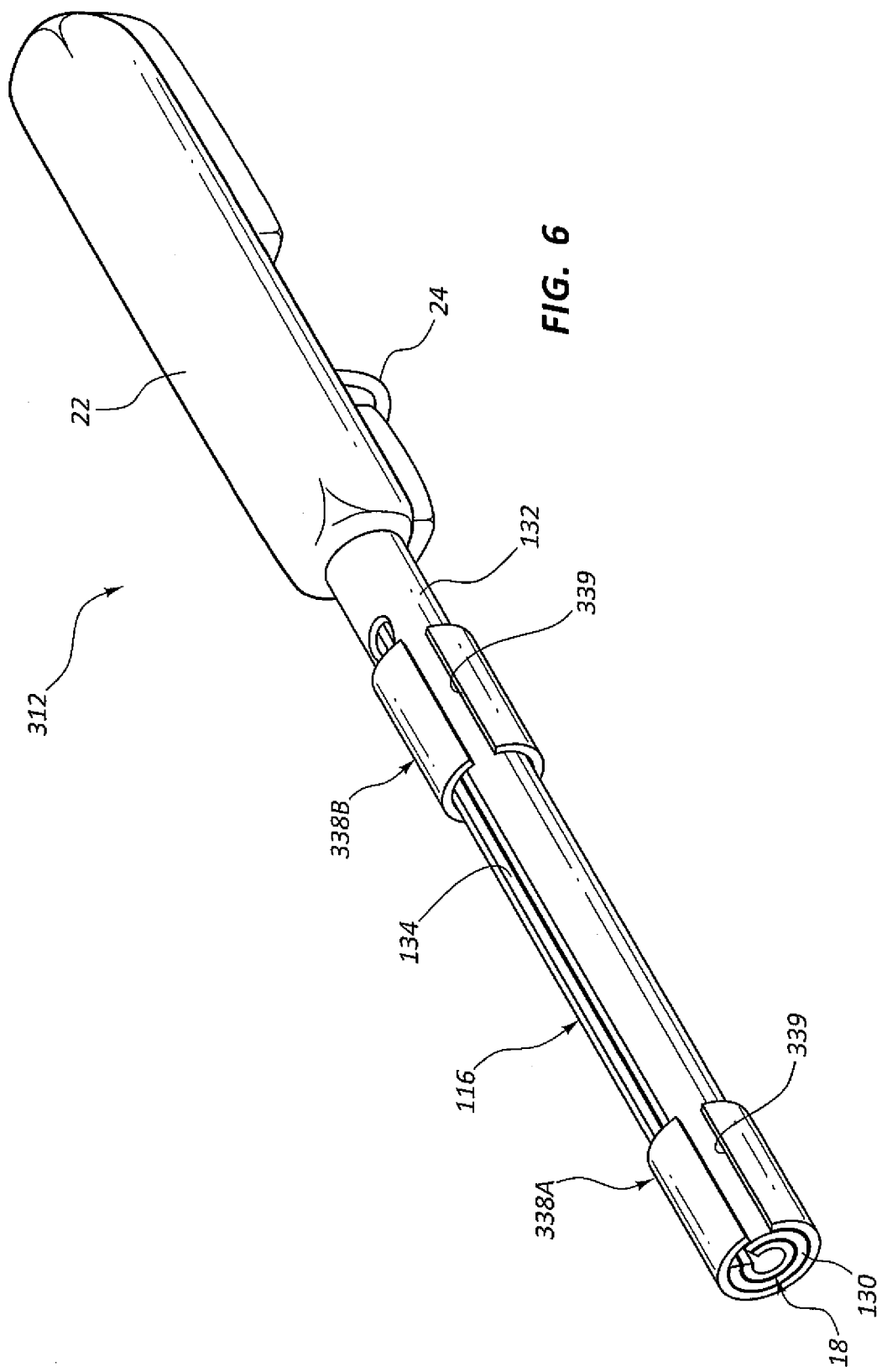
FIG. 6 is a perspective view of another example sealing plug delivery device in accordance with the present disclosure.

FIG. 6 shows another example sealing plug delivery device 312 that includes multiple locking members 338A, 338B positioned at spaced apart locations along a length of the carrier tube 116. The locking members 338A, 338B control access to the tube slot 134 at spaced-apart locations along a length of the tube slot 134. The locking members 338A, 338B may be separately operable to align a locking slot 339 of each of the locking members with the tube slot 134. FIG. 6 shows the locking slots 339 rotated out of alignment with the tube slot 134. The locking members 338A, 338B may be rotated into alignment with the tube slot 134 to provide lateral access through the tube slot 134 and into, for example, the plug slot 144 and the plug lumen 46. The locking members 338A, 338B may be independently operable or may rotate concurrently.

The locking members 338A, 338B may be positioned at opposite ends of the tube slot 134. For example, the locking member 338A may be positioned at the distal end portion 130 and the locking member 338B may be positioned at the proximal end portion 132 (e.g., adjacent to the proximal end 135 of the tube slot 134). The locking members 338A, 338B may be positioned at other locations. Furthermore, more than two locking members may be used to control access to the tube slot 134.

Referring now to FIGS. 7A and 7B, another example sealing plug delivery device 412 is shown including a carrier tube 416 and a sealing plug 118. The carrier tube 416 includes distal and proximal end portions 430, 432, a tube slot 434, and a locking member 438. The locking member 438 may control access through a portion of the tube slot 434. Alternatively, the carrier tube 416 relies on a shape of the tube slot 434 along a length of the tube slot 434 to help maintain an elongate member such as vessel locator 14 within the carrier tube 416 rather than using a locking member.

The tube slot 434 is shown having an orientation along a length of the tube slot 434 that is nonparallel with a length dimension of the carrier tube 416. In some arrangements, the tube slot 434 may have a diagonal orientation. The shape of the tube slot 434 may be, for example, diagonal or helical, and may comprise a step feature or any other desired feature along its length that helps retain the vessel locator 14 within the carrier tube 416. In one example, the tube slot 434 has a diagonal shape or orientation that matches the diagonal shape/orientation of sealing plug 118 shown in FIG. 8B.

The sealing plug delivery device 412 may rotate while inserting the vessel locator 14 through the tube slot 434 and through the plug slot 144 into a plug lumen 146 of the sealing plug 118. In at least some arrangements, the elongate vessel locator 14 may first be inserted at the distal end portion 430 through the tube slot 434 and plug slot 144 into the plug lumen 146. The vessel locator 14 may then pass through the tube slot 434, moving in a proximal direction until reaching a proximal end 435. The orientation of the tube slot 434 may assist in holding the vessel locator 14 within the carrier tube 416 while the sealing plug delivery device 412 is advanced or withdrawn along the vessel locator 14.

The locking member 438 is shown as a two-way valve. The locking member 438 may include separate flexible portions 440A, 440B that independently move to provide access through the tube slot 434 in radially inward or radially outward directions. The locking member 438 may have a construction (e.g., length, width and thickness) that provide a desired amount of flexibility to control lateral access of the vessel locator into and out of the tube slot 434. Various other constructions are possible for a locking member that provides a one-way or two-way passage.

Referring now to FIGS. 10-16, an example method of sealing a vessel puncture using the sealing plug delivery device 12 is shown and described. The sealing plug delivery device 12 may be part of a tissue puncture closure device 10 that additionally includes a vessel locator 14. The tissue puncture closure device 10 may be used to seal a vessel puncture 92 of a vessel 90 that is accessible through a percutaneous puncture 98 of a tissue layer 96.

The method is initiated by positioning the vessel locator 14 through the percutaneous puncture 98 and vessel puncture 92 into a vessel lumen 94 of vessel 90. The vessel locator 14 may include distal and proximal end portions 50, 52 and an expandable member 54. The expandable member 54 may expand using any desired expansion method, including, for example, an inflation fluid or a mechanical expansion member. The vessel locator 14 may include a fixture or hub at the proximal end portion 52 that has a size and shape that limits advancing a sealing plug delivery device over that fixture. As such, the construction of sealing plug delivery device 12 advantageously laterally mounts to the vessel locator 14 at a location distal of the fixture at the proximal end portion 52.

With the vessel locator 14 advanced into the vessel lumen 94, the expandable member 54 is expanded and the vessel locator 14 is withdrawn to contact the expandable member 54 against an inner surface of the vessel 90 adjacent to the vessel puncture 92. The expandable member 54 acts as an anchor that helps the operator identify a location of the vessel puncture 92.

Figure 11:
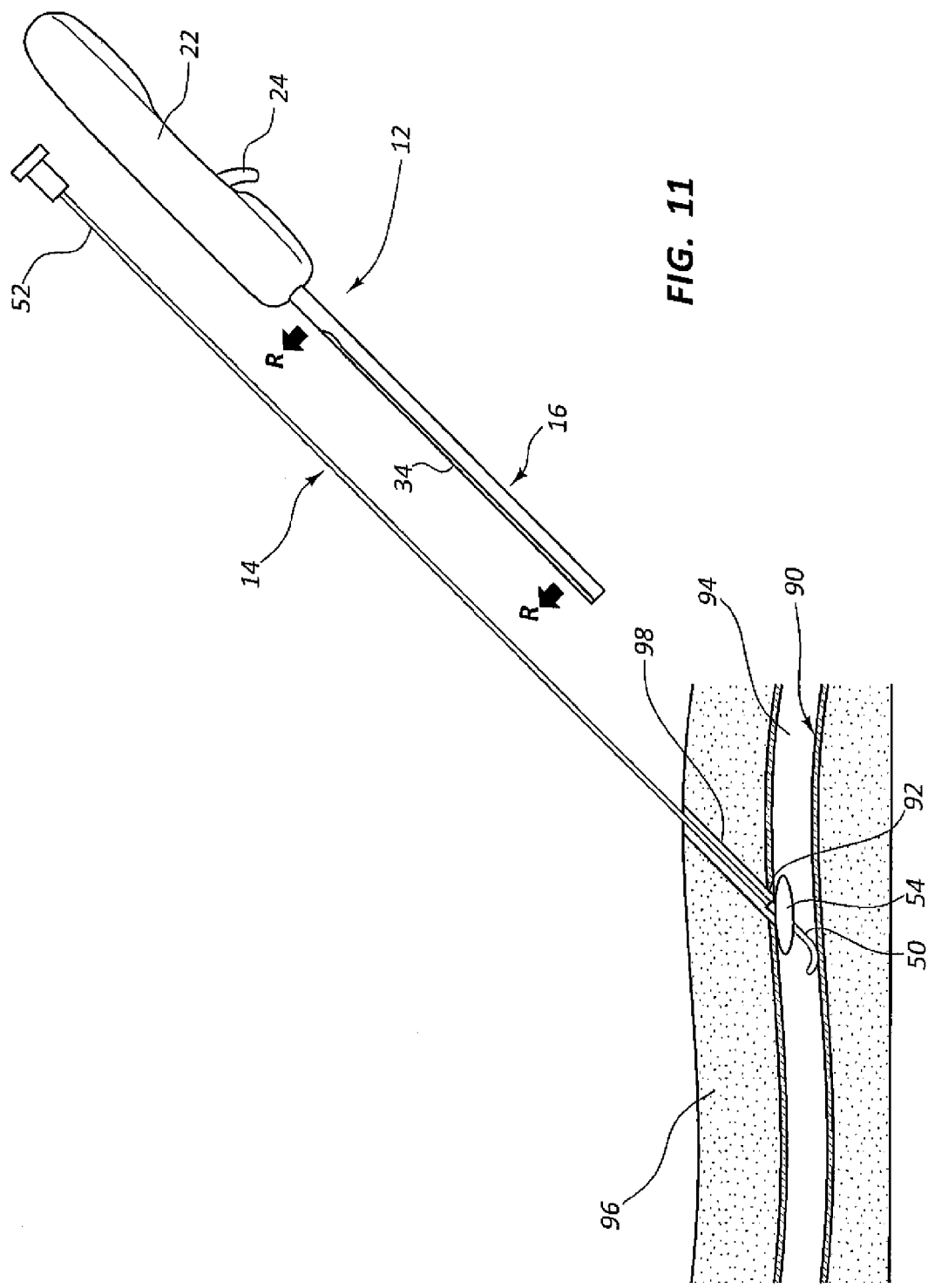
Figure 12:
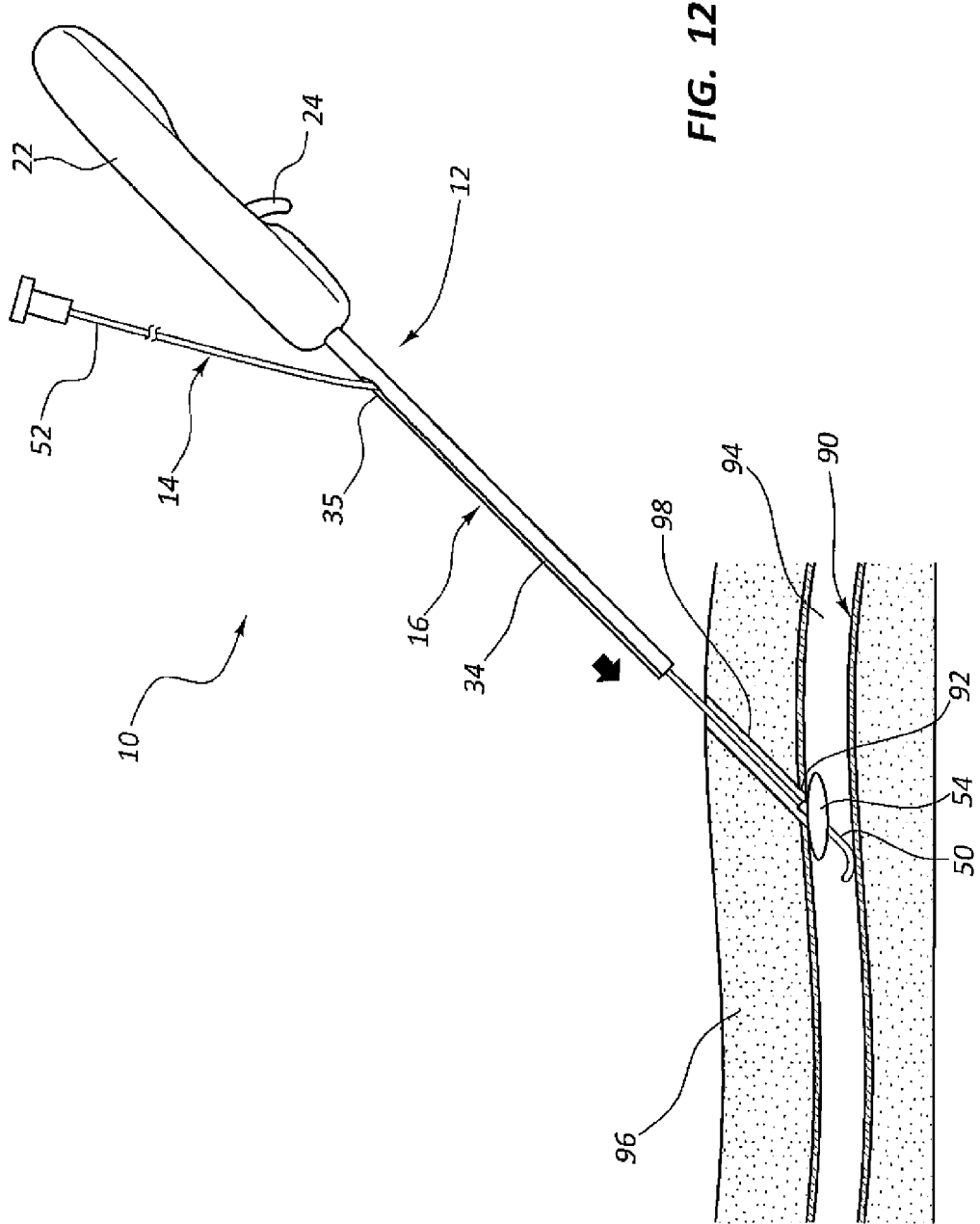

Referring now to FIG. 11, the sealing plug delivery device 12 is positioned adjacent to the vessel locator 14 with a vessel locator 14 aligned with the tube slot 34 and plug slot 44 of the sealing plug delivery device 12. The vessel locator 14 is moved laterally in a direction R through the tube slot 34 and plug slot 44 and into the plug lumen 46 as shown in FIG. 12. The locking member 38 may assist in holding the vessel locator 14 within the plug lumen 46.

Figure 13:
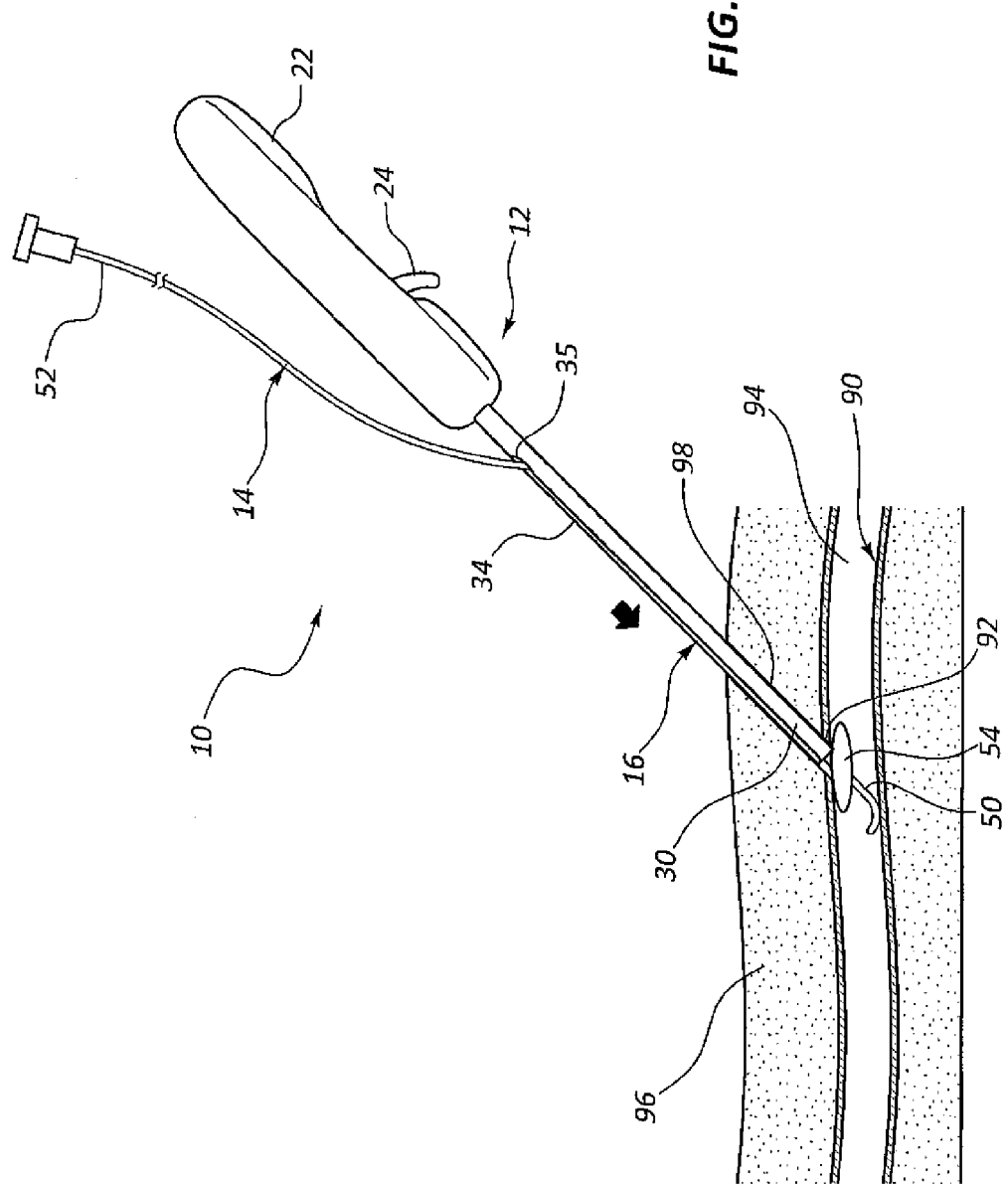
Figure 14:
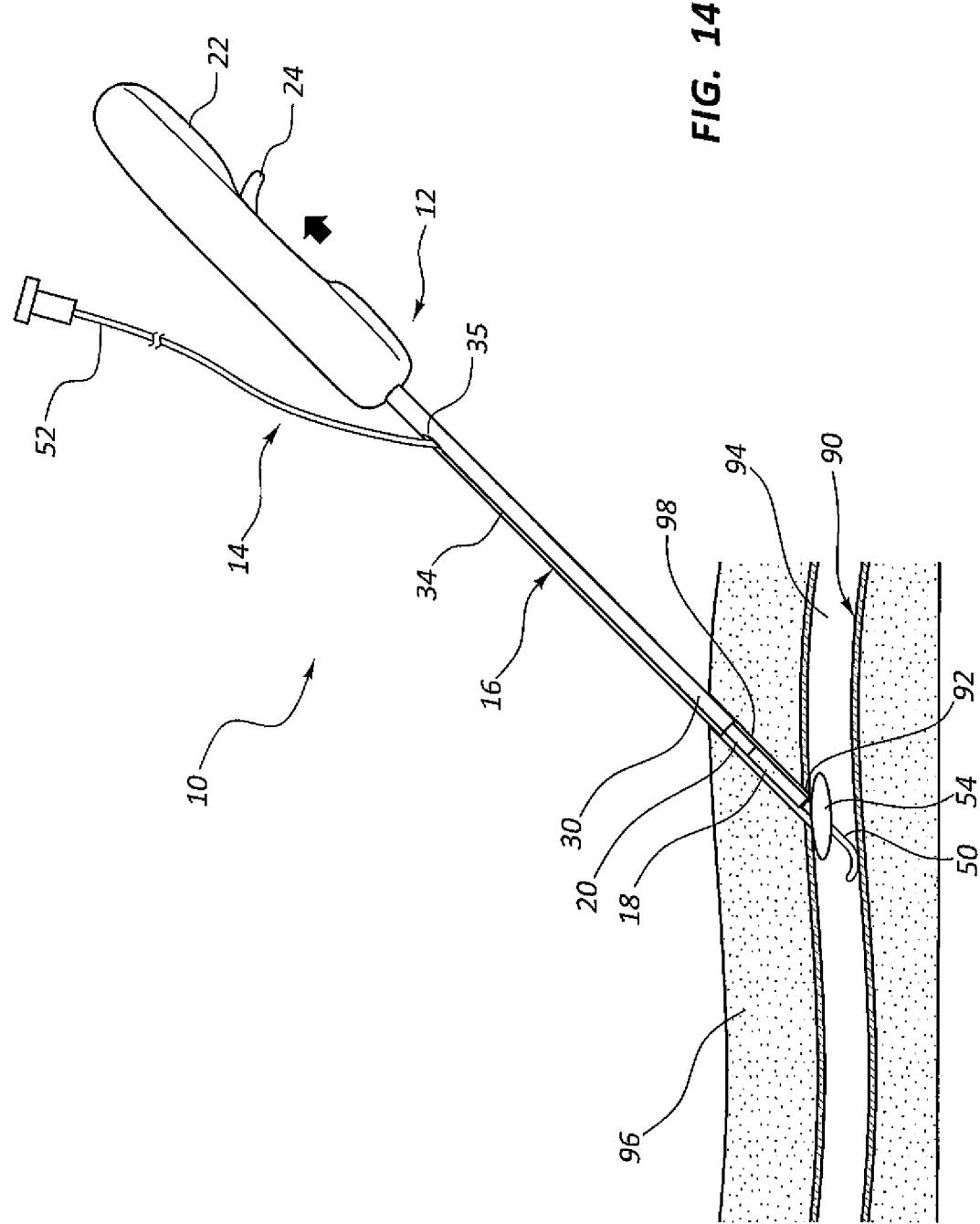

Referring to FIG. 13, the sealing plug delivery device 12 is advanced along the vessel locator 14 until the distal end portion 30 of the carrier tube 16 is positioned adjacent to the vessel puncture 92 along an exterior surface of the vessel 90. The sealing plug delivery device 12 is operated to deposit the sealing plug 18 adjacent to the vessel puncture 92. As discussed above, the sealing plug delivery device 12 may be operated to deposit the sealing plug 18 by either retracting the carrier tube 16 relative to the sealing plug 18 using the tube retractor 24, or by advancing the placement member 20 to eject the sealing plug 18 through the distal end of the carrier tube 16 using the tube retractor 24. FIG. 14 shows the tube retractor 24 operated in a proximal direction to deposit the sealing plug 18.

Figure 15:
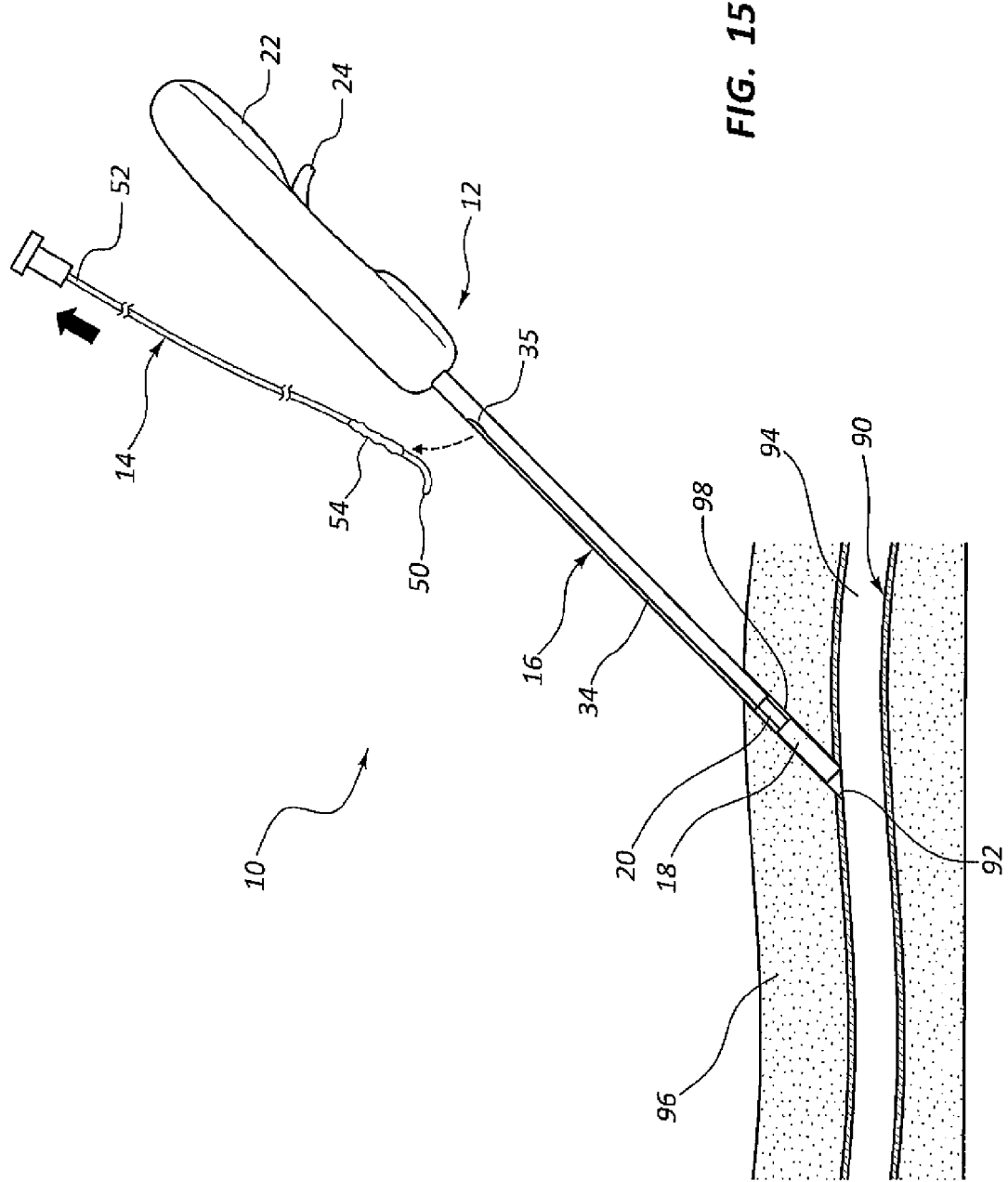

The sealing plug 18 may begin to expand upon being exposed to fluid such as blood that is present at the vessel puncture 92. The expandable member 54 may then be reduced in size and retracted through the sealing plug 18 as shown in FIG. 15. The vessel locator 14 may be independently withdrawn through the sealing plug 18 and sealing plug delivery device 12. Alternatively, the vessel locator 14 and sealing plug delivery device 12 are withdrawn concurrently out of the patient. In at least some examples, the sealing plug delivery device 12 is maintained in the axial position shown in FIG. 15 with the placement member 20 holding the sealing plug 18 in a fixed axial position while the vessel locator 14 is at least partially removed to limit dislodging of the sealing plug 18 from its position adjacent to the vessel puncture 92.

FIG. 16 shows the tissue puncture closure device 10 withdrawn from the patient and the sealing plug 18 remaining within the percutaneous puncture 98 adjacent to the vessel puncture 92 to seal the vessel puncture 92.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   a vessel locator comprising an expandable member;
   a sealing plug delivery member, comprising:
      a carrier tube having a distal end and a side opening, the side opening extending proximally from the distal end along at least a portion of a length of the carrier tube to provide lateral insertion of the vessel locator into an interior of the carrier tube;
      a sealing plug having a lumen and a slot extending from a distal end to a proximal end of the sealing plug, the slot providing lateral access of the vessel locator into the lumen;
      a locking member operable to retain the vessel locator within the sealing plug delivery member;
   wherein the locking member rotates external to the carrier tube between a first rotated position covering at least a portion of one of the side opening of the carrier tube and the slot of the sealing plug and a second rotated position removed from covering the side opening and slot, the locking member being longitudinally repositionable relative to the carrier tube while in the first rotated position, the locking member configured to rotate around a longitudinal axis of the sealing plug, the locking member being positionable along a length of the carrier tube while in the first rotated position.

2. The tissue puncture closure device of claim 1, wherein the sealing plug delivery member further comprises an actuator operable to deposit the sealing plug adjacent to a vessel puncture to seal the vessel puncture, wherein the actuator retracts the carrier tube relative to the sealing plug to deposit the sealing plug adjacent to the vessel puncture.

3. The tissue puncture closure device of claim 1, wherein the sealing plug delivery member further comprises an actuator operable to deposit the sealing plug adjacent to a vessel puncture to seal the vessel puncture, wherein the actuator advances the sealing plug out of the carrier tube to deposit the sealing plug adjacent to the vessel puncture.

4. The tissue puncture closure device of claim 1, wherein the locking member includes a deflectable member positioned at the side opening.

5. The tissue puncture closure device of claim 1, wherein the side opening and slot are aligned radially.

6. The tissue puncture closure device of claim 1, wherein the slot has a non-linear shape along a length of the sealing plug.

7. The tissue puncture closure device of claim 1, wherein the slot has a helical shape along a length of the sealing plug.

8. The tissue puncture closure device of claim 1, wherein the slot extends diagonally along a length of the sealing plug.

9. The tissue puncture closure device of claim 1, wherein the locking member includes a one-way opening.

10. The tissue puncture closure device of claim 1, wherein the locking member is positioned at the distal end of the carrier tube.

11. A tissue puncture closure device, comprising:
   a vessel locator comprising an expandable member;
   a sealing plug delivery member, comprising:
      a carrier tube having a distal end and a side opening, the side opening extending proximally from the distal end along at least a portion of a length of the carrier tube to provide lateral insertion of the vessel locator into an interior of the carrier tube;
      a sealing plug having a lumen and a slot extending from a distal end to a proximal end of the sealing plug, the slot providing lateral access of the vessel locator into the lumen;
      a locking member operable to retain the vessel locator within the sealing plug delivery member;
   wherein the slot has a non-linear shape along a length of the sealing plug.

12. The tissue puncture closure device of claim 11, wherein the slot has a helical shape along a length of the sealing plug.

13. A tissue puncture closure device, comprising:
   a vessel locator comprising an expandable member;
   a sealing plug delivery member, comprising:
      a carrier tube having a distal end and a side opening, the side opening extending proximally from the distal end along at least a portion of a length of the carrier tube to provide lateral insertion of the vessel locator into an interior of the carrier tube;
      a sealing plug having a lumen and a slot extending from a distal end to a proximal end of the sealing plug, the slot providing lateral access of the vessel locator into the lumen;
      a locking member operable to retain the vessel locator within the sealing plug delivery member;
   wherein the slot extends diagonally along a length of the sealing plug.

14. A tissue puncture closure device, comprising:
   a vessel locator comprising an expandable member;

a sealing plug delivery member, comprising:
- a carrier tube having a distal end and a side opening, the side opening extending proximally from the distal end along at least a portion of a length of the carrier tube to provide lateral insertion of the vessel locator into an interior of the carrier tube;
- a sealing plug having a lumen and a slot extending from a distal end to a proximal end of the sealing plug, the slot providing lateral access of the vessel locator into the lumen;
- a locking member operable to retain the vessel locator within the sealing plug delivery member;
- wherein the locking member rotates external to the carrier tube between a first rotated position covering at least a portion of one of the side opening of the carrier tube and the slot of the sealing plug and a second rotated position removed from covering the side opening and slot, the locking member being longitudinally slidable along a length of the carrier tube while in the first rotated position, the locking member being rotatable around a longitudinal axis of the sealing plug, the sealing plug being movable relative to the vessel locator while the locking member is in the first rotated position.

15. The tissue puncture closure device of claim 14, wherein the sealing plug delivery member further comprises an actuator operable to deposit the sealing plug adjacent to a vessel puncture to seal the vessel puncture, wherein the actuator retracts the carrier tube relative to the sealing plug to deposit the sealing plug adjacent to the vessel puncture.

16. The tissue puncture closure device of claim 14, wherein the sealing plug delivery member further comprises an actuator operable to deposit the sealing plug adjacent to a vessel puncture to seal the vessel puncture, wherein the actuator advances the sealing plug out of the carrier tube to deposit the sealing plug adjacent to the vessel puncture.

17. The tissue puncture closure device of claim 14, wherein the locking member includes a deflectable member positioned at the side opening.

18. The tissue puncture closure device of claim 14, wherein the side opening and slot are aligned radially.

19. The tissue puncture closure device of claim 14, wherein the slot has a non-linear shape along a length of the sealing plug.

20. The tissue puncture closure device of claim 14, wherein the slot has a helical shape along a length of the sealing plug.

21. The tissue puncture closure device of claim 14, wherein the slot extends diagonally along a length of the sealing plug.

22. The tissue puncture closure device of claim 14, wherein the locking member includes a one-way opening.

23. The tissue puncture closure device of claim 14, wherein the locking member is positioned at the distal end of the carrier tube.

* * * * *